(12) United States Patent
Steinbacher

(10) Patent No.: US 10,132,747 B2
(45) Date of Patent: Nov. 20, 2018

(54) ABSORPTION SPECTROMETER

(71) Applicant: Siemens Aktiengesellschaft, Munich (DE)

(72) Inventor: Franz Steinbacher, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 15/537,052

(22) PCT Filed: Dec. 2, 2015

(86) PCT No.: PCT/EP2015/078290
§ 371 (c)(1),
(2) Date: Jun. 16, 2017

(87) PCT Pub. No.: WO2016/096416
PCT Pub. Date: Jun. 23, 2016

(65) Prior Publication Data
US 2018/0003624 A1    Jan. 4, 2018

(30) Foreign Application Priority Data

Dec. 17, 2014  (DE) .................. 10 2014 226 323
Dec. 22, 2014  (DE) .................. 10 2014 226 845

(51) Int. Cl.
*G01J 5/02*       (2006.01)
*G01N 21/3504*    (2014.01)
(Continued)

(52) U.S. Cl.
CPC .......... *G01N 21/3504* (2013.01); *G01J 3/108* (2013.01); *G01J 3/433* (2013.01);
(Continued)

(58) Field of Classification Search
CPC ... H01S 3/1398; H01S 5/141; G01N 21/3504; G01N 2021/1793; G01N 21/1702;
(Continued)

(56) References Cited

U.S. PATENT DOCUMENTS 3,921,099 A * 11/1975 Abrams ................ H01S 3/1398
372/32
4,441,815 A *  4/1984 Izumi ..................... G01J 3/433
250/373

(Continued)

FOREIGN PATENT DOCUMENTS

DE         60310712 T2     10/2007
DE       602005003337 T2    9/2008
(Continued)

*Primary Examiner* — Kiho Kim
(74) *Attorney, Agent, or Firm* — Cozen O'Connor

(57) ABSTRACT

An absorption spectrometer which measures a gas component concentration in a measured gas and which operates via wavelength modulation spectroscopy, wherein the light wavelength of a wavelength-tunable light source is periodically varied over a gas component absorption line of interest and simultaneously sinusoidally modulated with a high frequency and a low amplitude signal, and wherein the measurement signal of a detector is demodulated in a phase-sensitive manner at the frequency and/or a harmonic of the frequency and further analyzed, where modulation starts in each period or each n-th period with the frequency in a time interval before the beginning of the time function and is performed with a higher amplitude than during the time function to demodulate the measurement signal in a phase-synchronous manner, where a device provided for the phase-sensitive demodulation is synchronized during the time interval such that a cable for transmitting synchronization signals is no longer necessary.

10 Claims, 2 Drawing Sheets

(51) Int. Cl.
  *G01N 21/39* (2006.01)
  *G01J 3/433* (2006.01)
  *G01J 3/10* (2006.01)

(52) U.S. Cl.
  CPC ............ *G01J 3/4338* (2013.01); *G01N 21/39* (2013.01); *G01N 2021/399* (2013.01); *G01N 2201/068* (2013.01); *G01N 2201/0612* (2013.01)

(58) Field of Classification Search
  CPC ............ G01N 29/222; G01N 29/2425; G01N 29/2462; G01N 29/30; G01N 2021/1704; G01N 2291/02408; G01N 2291/02872; G01N 21/39; G01N 2021/391
  See application file for complete search history.

(56) References Cited

U.S. PATENT DOCUMENTS

| | | | | |
|---|---|---|---|---|
| 5,723,864 | A * | 3/1998 | Atkinson | G01N 21/3504 250/339.13 |
| 5,767,976 | A * | 6/1998 | Ankerhold | G01N 21/3504 250/338.5 |
| 7,132,661 | B2 * | 11/2006 | May | G01J 3/4338 250/339.13 |
| 7,636,153 | B2 * | 12/2009 | Willing | G01N 21/1702 250/339.13 |
| 8,934,100 | B2 * | 1/2015 | Liu | G01N 21/39 356/437 |
| 9,052,274 | B2 * | 6/2015 | Depenheuer | G01J 3/28 |
| 9,360,417 | B2 * | 6/2016 | Disch | G01N 21/3504 |
| 9,453,765 | B2 * | 9/2016 | Depenheuer | G01J 3/42 |
| 9,546,989 | B2 * | 1/2017 | Bitter | G01J 3/28 |
| 9,752,931 | B2 * | 9/2017 | Waldmann | G01J 3/0205 |
| 9,772,277 | B2 * | 9/2017 | Muramatsu | G01N 21/39 |
| 2002/0194897 | A1 * | 12/2002 | Arnott | G01N 21/1702 73/23.31 |
| 2005/0046852 | A1 | 3/2005 | Larking et al. | |
| 2007/0131882 | A1 | 6/2007 | Richman | |
| 2009/0201507 | A1 | 8/2009 | Kluczynski et al. | |
| 2011/0181879 | A1 * | 7/2011 | Chen | G01N 21/274 356/318 |
| 2012/0241622 | A1 * | 9/2012 | Heyne | G01N 21/031 250/339.13 |
| 2013/0135619 | A1 * | 5/2013 | Hirata | G01N 21/39 356/409 |
| 2015/0042991 | A1 | 2/2015 | Hankiewicz et al. | |
| 2015/0268095 | A1 | 9/2015 | Kovacich et al. | |
| 2015/0338342 | A1 * | 11/2015 | Muramatsu | G01N 21/39 356/409 |

FOREIGN PATENT DOCUMENTS

| | | |
|---|---|---|
| DE | 102012202893 B3 | 1/2013 |
| DE | 102013201459 A1 | 7/2014 |
| EP | 2072979 A1 | 6/2009 |

\* cited by examiner

ABSORPTION SPECTROMETER

CROSS-REFERENCE TO RELATED APPLICATIONS

This is a U.S. national stage of application No. PCT/EP2015/078290 filed 2 Dec. 2015. This application claims the priority of German application no. 102014226323.9 filed Dec. 17, 2014 and German application no. 102014226845.1 filed Dec. 22, 2014, the content of which are incorporated by reference in their entirety.

BACKGROUND OF THE INVENTION

1. Field of the Invention

The invention relates to an absorption spectrometer for measuring the concentration of a gas component in a measured gas based on wavelength modulation spectroscopy (WMS).

2. Description of the Related Art

DE 10 2013 201 459 A1 discloses an exemplary absorption spectrometer.

In "in-line" or "in-situ" measurement, for example, in the process manufacturing industry or the energy industry, the measurement volume is often formed by a gas conduit, such as a pipe, or a flue, carrying the measured gas. The light source and the detector are then arranged at different sites of the process plant, for which purpose, the spectrometer is subdivided into two partial devices, specifically a transmitter with the light source and a receiver containing the detector. These partial devices are connected to one another via a special coupling line so that they can function as an overall device. In particular, via the coupling line, a system clock signal is transmitted to perform synchronization between the transmitter and the receiver such that the measurement signal generated by the detector can be demodulated in a manner that is phase-sensitive to its modulation.

The provision and laying of such coupling lines, in particular in an industrial environment, is associated with a corresponding effort.

SUMMARY OF THE INVENTION

The underlying object of the invention is therefore to lessen the equipment and assembly effort with absorption spectrometers, particularly within in situ absorption spectrometers.

This and other objects and advantages are achieved in accordance with the invention by an absorption spectrometer having a wavelength-tunable light source, a modulation device that periodically varies the wavelength of the light of the tunable light source over an absorption line of interest of the gas component in accordance with a specified time function and simultaneously sinusoidally modulates the light with a high frequency and a small amplitude signal, a detector that detects the intensity of the light after passing through the measured gas, and an evaluating device which contains means for phase-sensitive demodulation of a measurement signal generated by the detector at the frequency and/or one of its harmonics.

In accordance with the invention, the modulation device is further configured to start the modulation in each period or each n-th period with the frequency in a time interval before the beginning of the time function and to perform the modulation at a larger amplitude than during the time function, and the evaluating device is configured to perform a synchronization of the means for phase-sensitive demodulation during the time interval based on the frequency contained in the measurement signal.

The synchronization between transmitter and receiver therefore advantageously occurs via sinusoidal modulation of the light occurring in the time interval before the beginning of the time function serving for wavelength-dependent scanning of the absorption line. Herein, the modulation amplitude is relatively large, such that a sufficiently large signal-to-noise ratio is achieved to ensure reliable synchronization, even with poor transmission conditions, such as due to aerosols in the measured gas. As will be described below in more detail, as distinct therefrom, the scanning of the absorption line of the measured gas components of interest requires a relatively small amplitude of the overlaid sinusoidal modulation to obtain an optimum measurement result.

The synchronization of the means for phase-sensitive demodulation of the measurement signal preferably occurs via the output signal of a phase-locked loop with a controllable sinusoidal oscillator. The measurement signal is supplied to the input of the phase-locked loop via a controllable switch that is closed during the time interval for performing the synchronization, such that the sinusoidal oscillator is regulated phase-exactly with the frequency of the sinusoidal modulation contained in the measurement signal. The sinusoidal oscillator receives its control signal via a holding element that is activated outside the time interval such that the regulation is interrupted and the sinusoidal oscillator continues to oscillate freely with the last regulated frequency.

The time point for the start of the synchronization of the means for phase-sensitive demodulation of the measurement signal can be determined from the shape of the measurement signal. Thus, for example, through bandpass filtration of the measurement signal and subsequent monitoring of the bandpass filtered measurement signal, exceeding a threshold value can be detected if the sinusoidal-shaped modulation occurs at the larger amplitude. Preferably, in the event that the time function is ramp-shaped or that the wavelength-tunable light source is triggered at the beginning and/or end of each period with a burst signal, the falling ramp flank or the burst signal is detected in the measurement signal to perform the synchronization after a pre-set time following thereon. Herein, a free-running counter that is reset on every detection of a falling ramp flank or a burst signal can provide the time point for the synchronization on reaching a pre-determined count value.

In order to be able to detect the falling ramp flank or the burst signal reliably in the measurement signal, it is advantageously differentiated in advance so that the steep flank of the ramp signal or the flanks of the burst signal appear as well resolved peaks. In particular, by counting the peaks the beginning and the end of the burst signal can be reliably determined.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention will now be described making reference to the drawings based upon examples, in which.

DETAILED DESCRIPTION OF THE EXEMPLARY EMBODIMENTS

Figure 1:
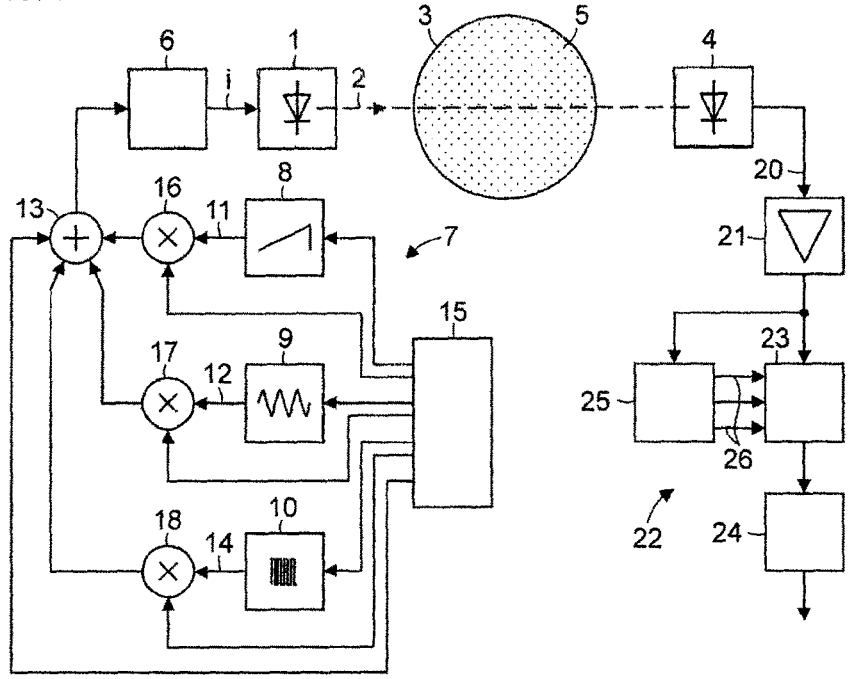
FIG. 1 is a schematic representation of an exemplary embodiment of the absorption spectrometer in accordance with the invention.

FIG. 1 shows an absorption spectrometer with a wavelength-tunable light source 1 as a laser diode, the light 2 of which is guided in the form of a light beam through a measurement volume 3 to a detector 4 that detects the light intensity. The measurement volume 3 can be a measuring cell that contains a measured gas 5 and in which the concentration of at least one gas component of interest is to be measured. In the case of an in situ measurement, the measurement volume 3 can consist of a process gas line, such as a pipe or a flue, through which the measured gas 5 flows. The laser diode 1 and the detector 4 are then typically arranged in two different measurement heads that are mounted on the process gas conduit at diametrically opposite sites via flange connections and conduct the light through windows into the process gas conduit or receive it therefrom.

The laser diode 1 is controlled from a controllable current source 6 with an injection current i, where the intensity and the wavelength of the light 2 generated depend on the current i and the operating temperature of the laser diode 1. The current source 6 is triggered by a modulation device 7 that contains a first signal generator 8, a second signal generator 9 and a third signal generator 10. The first signal generator 8 periodically generates a pre-determined, preferably ramp-shaped time function 11 to scan in a wavelength-dependent manner a selected absorption line of the gas components of interest of the measured gas 5 with the corresponding modulated light 2. The second signal generator 9 generates a sinusoidal signal 12 of frequency f with which, in a summing element 13, the ramp-shaped time function 11 is modulated. The third signal generator 10 generates a burst signal 14 with which the injection current i can be switched on and off several times in succession. The temporal sequence of the signals 11, 12, 14 and their respective offset for the periodic control of the laser diode 1 is controlled by a control unit 15 that also sets the signal sizes (amplitudes) via multiplier units 16, 17, 18.

Figure 2:
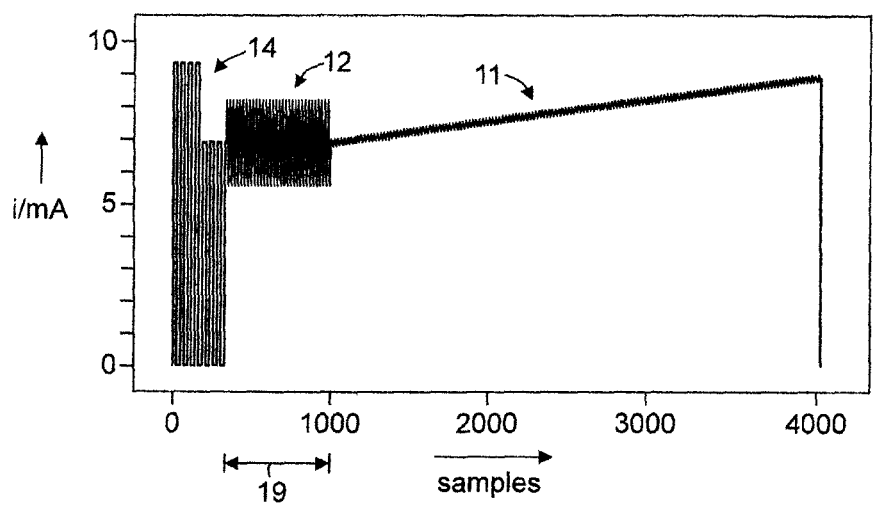
FIG. 2 is an exemplary graphical plot of the shape of the current for controlling the wavelength-tunable light source during a triggering period in accordance with the invention.

FIG. 2 shows an exemplary graphic plot of the shape of the injection current i of the laser diode 1 during a triggering period. Since the intensity and wavelength of the generated light 2 have a corresponding shape and a selected absorption line of the gas components of interest of the measured gas 5 is to be scanned, scanning time points are given on the abscissa.

At the start of the period, the current i is switched on and off several times with the burst signal 14, where in two successive time portions, two different switch-on current strengths are used that are selected such that the resultant wavelength of the light 2 lies outside the wavelength regions of the gas components to be measured and of other infrared-active gas components of the measured gas 5. The period can also be defined such that the burst signal 14 is generated at the end of the period or one of the two time portions lies at the start and the other at the end of the period. The burst signal 14 serves to normalize the measurement, as is known, for example, from the aforementioned DE 10 2013 201 459 A1.

Following the switching off of the burst signal 14, the current i is modulated during a pre-set time interval 19 by the sinusoidal signal 10 with the frequency f and a relatively large amplitude. Subsequently, the amplitude of the sinusoidal modulation is lessened and the current is additionally varied with the ramp-shaped time function 11. Accordingly, the wavelength of the generated light 2 is also varied linearly, where a small part of the light 2 is absorbed by the infrared-active gas components of the measured gas 1 in a wavelength-dependent manner. With this, it is possible to scan the absorption line of the gas components of interest in the measured gas 5 in a wavelength-dependent manner. The profile of the absorption line is not linear and the wavelength of the light 2 is additionally modulated sinusoidally during the relatively slow scanning of the absorption line with a high frequency f and a small amplitude (wavelength modulation spectroscopy, or WMS). As a result, higher order harmonics are also created in the light intensity detected by the detector 4. The evaluation of these higher, preferably second order, harmonics by phase-sensitive lock-in technology is particularly advantageous if low concentrations of the gas components of interest are to be measured because, in this way, noise can be better filtered out of the measurement signal.

As FIG. 1 shows, the detector 4 generates a measurement signal 20 corresponding to the detected light intensity that is amplified in an amplifier 21 and is normalized based on the light intensities detected at the sites of the burst signal 14. The amplified measurement signal 20 is subsequently evaluated in an evaluating device 22. The evaluating device 22 contains means 23 for phase-sensitive demodulation of the measurement signal 20 at the frequency 2f and a computation device 24 in which the frequency 2f signal components are evaluated to determine the concentration of the gas components of interest of the measured gas 5.

In order for the phase-sensitive detection of the measurement signal 20 to occur synchronously with its modulation, the means 23 for phase-sensitive demodulation are synchronized during the time interval 19 based on the frequency f contained in the measurement signal 20. For this purpose, the evaluating device 22 contains a synchronizing unit 25 that generates control signals 26 for synchronizing the means 23 from the measurement signal 20.

Figure 3:
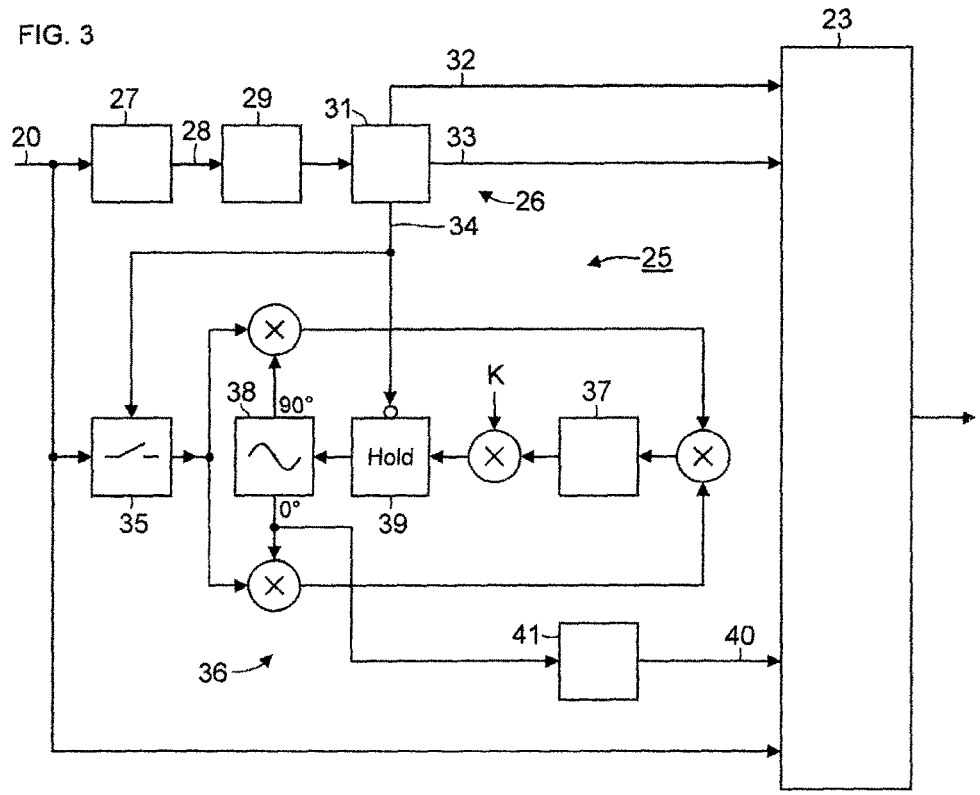
FIG. 3 is an exemplary schematic representation of a synchronization device for synchronizing the means for phase-sensitive demodulation in accordance with the invention.
Figure 4:
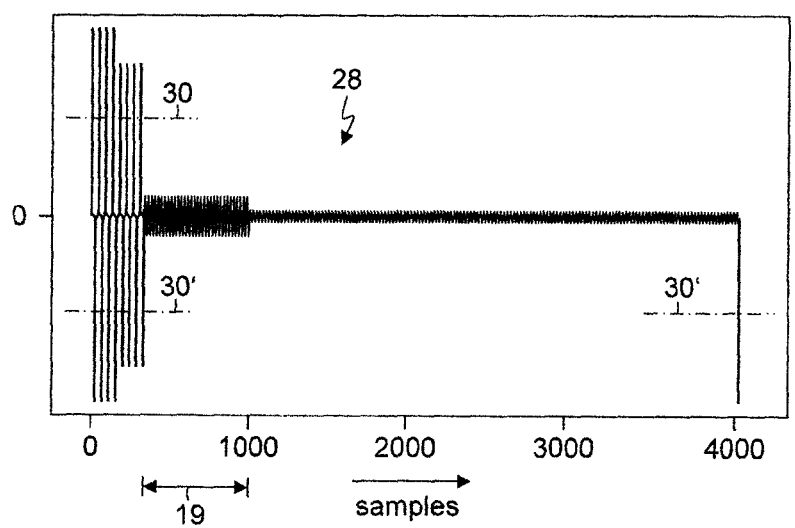
FIG. 4 is an exemplary graphical plot of the differentiated measurement signal of the detector in accordance with the invention.

FIG. 3 shows an example of the synchronizing device 25 in which the amplified measurement signal 20 is differentiated in a differentiating unit 27, such that a signal 28 shown in FIG. 4 is obtained. A downstream threshold value detector 29 detects whether the peaks of the differentiated measurement signal resulting from the burst signal 14 or the falling flank of the ramp-shaped time function 11 exceed a positive threshold value 30 or fall below a negative threshold value 30', and resets a counter 31. Following the last burst peak or, if no burst signal is used, following the peak of the falling flank of the ramp-shaped time function 11, the counter 31 begins to count upward until the next burst or until the next flank. Dependent upon the counter value, the control signals 26 are then generated, where these dependencies are parameterizable. In the illustrated exemplary embodiment, the control signals 26 comprise a first control signal 32 for the time and duration of the burst signal 14, a second control signal 33 for the time and duration of the time function 11 and a third control signal 34 that marks the pre-determined time interval 19 in which the modulation of the injection current i occurs via the sinusoidal signal 10 with the frequency f and with a relatively large amplitude. With this third control signal 34, a controllable switch 35 is closed for the duration of the pre-determined time interval 19 to feed the amplified measurement signal 20 to a phase-locked loop (PLL) 36. The phase-locked loop 36 consists in the exemplary embodiment shown of a Costas loop with a loop filter 37 with the output signal of which a sinusoidal oscillator 38, in this case a DDS-VCO (direct digital synthesis; voltage-controlled oscillator) is controlled. The amplification of the phase-locked loop 36 can be set through multiplication of the output of the loop filter 37 by a factor K. Arranged between the loop filter 37 and the sinusoidal oscillator 38 is a holding element 39 that is controlled inverted as compared with the switch 35.

For the duration of the pre-set time interval 19, the switch 35 is closed and the holding element 39 is deactivated, such that the sinusoidal oscillator 38 is regulated phase-exactly with the frequency f contained in the measurement signal 20. The sinusoidal signal generated by the sinusoidal oscillator 38 passes through a phase-shifter 41 before being supplied as the output signal 40 of the phase-locked loop 36 to the means 23 for phase-sensitive demodulation of the measurement signal 20. The measurement signal 20 is filtered during its amplification and the subsequent demodulation at the frequency nf. As a result, a phase adaptation that takes account of different phase responses of the filters occurs in the phase shifter 41. The output signal 40 of the phase-locked loop 36 is identical, with respect to frequency and phase, to the sinusoidal modulation signal 12, such that the amplified measurement signal 20 can be demodulated phase-exactly to the modulation. The respective demodulation frequency nf can be derived directly from the output signal 40 by frequency multiplication. It is possible, for the purpose of a multiple modulation of the light 2 generated, additionally to modulate the ramp-shaped time function 11 with further sinusoidal signals, the frequencies of which are derived from the frequency f of the modulation signal 12. In this case, the measurement signal 20 can also be demodulated without difficulty through derivation of the respectively desired demodulation frequency/frequencies from the output signal 40 phase-exactly.

The amplitude of the sinusoidal modulation signal 12 is relatively large during the time interval 19. As a result, the signal-to-noise ratio is sufficiently high to ensure a reliable synchronization, even with poor transmission conditions due, such as to smoke particles or dust in the measured gas 5.

For scanning the absorption line of the measured gas components of interest via the ramp-shaped time function 11, however, the amplitude of the overlaid sinusoidal modulation, i.e., the wavelength increase of the generated light 2 must be adapted to the width of the absorption line to be scanned and is, in practice, too low for the purpose of the synchronization. Thus, in the ideal case of a Lorentzian absorption curve, the 2f signal portion of the measurement signal 20 is a maximum with a modulation index (ratio of the spectral modulation amplitude to the half-width of the scanned absorption line) of 2.2.

Outside the pre-set time interval 19, the switch 35 is open and the holding element 39 is deactivated, such that the sinusoidal oscillator 38 oscillates freely in accordance with the output value last generated by the loop filter 37 and held by the holding element 39.

Thus, while there have been shown, described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. An absorption spectrometer for measuring a concentration of a gas component in a measured gas via wavelength modulation spectroscopy, the absorption spectrometer comprising:
    a wavelength-tunable light source;
    a modulation device which periodically varies a wavelength of light of the wavelength-tunable light source over an absorption line of interest of the gas component in accordance with a specified time function and simultaneously sinusoidally modulates the wavelength of light of the wavelength-tunable light source with a high frequency and low amplitude signal;
    a detector which detects an intensity of the light after passing through the measured gas; and
    an evaluating device which contains a demodulation device for phase-sensitive demodulation of a measurement signal generated by the detector at at least one of (i) a frequency of the measurement signal and (ii) an harmonic of the measurement signal;
    wherein the modulation device is configured to start a modulation in each period or each n-th period with the frequency in a time interval before a beginning of the specified time function and perform the modulation at a larger amplitude than during the specified time function; and
    wherein the evaluating device is configured to perform a synchronization of the demodulation device for phase-sensitive demodulation during the time interval based on the frequency contained in the measurement signal.

2. The absorption spectrometer as claimed in claim 1, wherein the evaluating device comprises a phase-locked loop with a controllable sinusoidal oscillator;
    wherein the measurement signal is supplied to the phase-locked loop on an input side via a controllable switch which is closed to implement the synchronization of the demodulation device for phase-sensitive demodulation;
    wherein the output signal of the phase-locked loop is fed to the demodulation device for phase-sensitive demodulation; and
    wherein the control signal for the sinusoidal oscillator is supplied to said sinusoidal oscillator via a holding element which is activated outside the time interval in which the synchronization occurs.

3. The absorption spectrometer as claimed in claim 2, wherein the evaluating device is configured to detect the falling ramp flank in the measurement signal with a ramp-shaped time function in order to, after a pre-set time following thereafter, perform the synchronization of the demodulation device for phase-sensitive demodulation.

4. The absorption spectrometer as claimed in claim 2, wherein the modulation device includes a modulator which modulates the light at at least one of (i) a start and (ii) an end of each period with a burst signal, and wherein the evaluating device is further configured to detect the burst signal in the measurement signal in order to, after a pre-set time following thereafter, perform the synchronization of the demodulation device for phase-sensitive demodulation.

5. The absorption spectrometer as claimed in claim 1, wherein the evaluating device is configured to detect the falling ramp flank in the measurement signal with a ramp-shaped time function in order to, after a pre-set time following thereafter, perform the synchronization of the demodulation device for phase-sensitive demodulation.

6. The absorption spectrometer as claimed in claim 5, wherein the evaluating device comprises a free-running counter which, upon detecting a falling ramp flank or a burst signal is reset and, upon reaching a preset counter value, issues a time for the synchronization.

7. The absorption spectrometer as claimed in claim 5, wherein the evaluating device comprises a differentiating unit for differentiating the measurement signal, and wherein the falling ramp flank or flanks of the burst signal are detected in the differentiated measurement signal.

8. The absorption spectrometer as claimed in claim 1, wherein the modulation device includes a modulator which modulates the light at at least one of (i) a start and (ii) an end of each period with a burst signal, and wherein the evaluating device is further configured to detect the burst signal in the measurement signal in order to, after a pre-set time following thereafter, perform the synchronization of the demodulation device for phase-sensitive demodulation.

9. The absorption spectrometer as claimed in claim 8, wherein the evaluating device comprises a free-running counter which, upon detecting a falling ramp flank or a burst signal is reset and, upon reaching a preset counter value, issues a time for the synchronization.

10. The absorption spectrometer as claimed in claim 8, wherein the evaluating device comprises a differentiating unit for differentiating the measurement signal, and wherein the falling ramp flank or flanks of the burst signal are detected in the differentiated measurement signal.

* * * * *